United States Patent
Shin et al.

(10) Patent No.: US 10,391,333 B2
(45) Date of Patent: Aug. 27, 2019

(54) TREATMENT APPARATUS USING PROTON AND ULTRASOUND AND METHOD OF TREATING CANCER USING THE SAME

(71) Applicant: ELECTRONICS AND TELECOMMUNICATIONS RESEARCH INSTITUTE, Daejeon (KR)

(72) Inventors: Dong-Ho Shin, Daejeon (KR); Sang Kyun Lee, Daejeon (KR); Seunghwan Kim, Daejeon (KR); Moon Youn Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/871,641

(22) Filed: Jan. 15, 2018

(65) Prior Publication Data

US 2018/0289979 A1    Oct. 11, 2018

(30) Foreign Application Priority Data

Apr. 10, 2017 (KR) ........................ 10-2017-0046239

(51) Int. Cl.
*A61N 5/10* (2006.01)
*A61N 7/02* (2006.01)
*A61B 8/08* (2006.01)
*A61B 5/00* (2006.01)

(52) U.S. Cl.
CPC ............ *A61N 5/1031* (2013.01); *A61B 8/085* (2013.01); *A61N 5/1039* (2013.01); *A61N 5/1067* (2013.01); *A61N 7/02* (2013.01); *A61B 5/0035* (2013.01); *A61B 8/08* (2013.01); *A61B 2562/0204* (2013.01); *A61N 2005/109* (2013.01); *A61N 2005/1087* (2013.01)

(58) Field of Classification Search
CPC .. A61N 5/1031; A61N 5/1039; A61N 5/1067; A61N 7/02; A61N 2005/1087; A61N 2005/109; A61B 5/0035; A61B 8/08
USPC ............................... 250/492.1, 492.2, 492.3
See application file for complete search history.

(56) References Cited

U.S. PATENT DOCUMENTS

| | | |
|---|---|---|
| 9,545,527 B2 | 1/2017 | Moskvin et al. |
| 2011/0101244 A1 | 5/2011 | Jung et al. |
| 2011/0147619 A1 | 6/2011 | Jung et al. |
| 2014/0061493 A1 | 3/2014 | Prieels et al. |
| 2017/0165504 A1* | 6/2017 | Dollinger ............. A61N 5/1048 |

OTHER PUBLICATIONS

Kazuhisa Nakajima et al., "Laser-Driven Very High Energy Electron/Photon Beam Radiation Therapy in Conjunction with a Robotic System", Applied Sciences, 2015, pp. 1-20, vol. 5.

* cited by examiner

*Primary Examiner* — Nicole M Ippolito (57) ABSTRACT

Provided are a treatment apparatus using proton and ultrasound and a method for treating cancer using the same. The treatment apparatus includes a proton generator configured to emit a proton beam to a tumor of a human body, an ultrasound generator configured to emit an ultrasonic beam to the tumor in a direction crossing an emission path of the proton beam, and a sensor configured to measure an acoustic signal generated during the emission of the proton beam.

15 Claims, 7 Drawing Sheets

TREATMENT APPARATUS USING PROTON AND ULTRASOUND AND METHOD OF TREATING CANCER USING THE SAME

CROSS-REFERENCE TO RELATED APPLICATIONS

This U.S. non-provisional patent application claims priority under 35 U.S.C. § 119 of Korean Patent Application No. 10-2017-0046239, filed on Apr. 10, 2017, the entire contents of which are hereby incorporated by reference.

BACKGROUND

The present disclosure herein relates to a treatment apparatus using proton and ultrasound and a method of treating cancer using the same, and more particularly, to a complex cancer treatment apparatus capable of treating and monitoring cancer and a method of treating cancer using the same.

Cancer treatment using proton can reduce a radiation dose that is unnecessary for normal tissues, so there are no sequalae after surgical procedures, when compared to typical radiation treatment. However, when a head and neck cancer recurs, it is difficult to treat the cancer by using the proton, and thus neutron treatment may be used instead of using the proton treatment. The neutron treatment uses a principle, in which, when an element (for example, boron) for catching the neutron is placed at a treatment region, beta rays or gamma rays, which are generated through the coupling between the element and the neutron, attack and destroy cancer tissue. When the neutron is used to treat the cancer, there may be several limitations. For example, since the neutron has no electric charge, it is difficult to control the neutron, unlike the proton. Also, the normal tissue may be easily exposed to the neutron, resulting in side effects.

Also, it is not easy to identify a dose or a depth profile of a particle beam through the proton treatment. When a dose distribution of the particle beam within the human body is not accurately identified, a treatment planning system may not accurately calculate a dose that would be exposed in the human body. Therefore, when the proton treatment is conducted, the treatment is performed with an additional margin for a planning target volume (PTV), taking into consideration of safety for patients.

Since a proton beam enters the human body as much as energy it has, transfers all the energy, and then is absorbed, it is impossible to predict an internal dose by measuring an exit dose and finding the distribution of the proton beam. At the beginning of the proton treatment, a positron emission tomography (PET) method was proposed, which measures a location at which pair annihilation of a positron occurs wherein the positron is produced by the interaction with an atom or a nucleus constituting the inside of the human body. However, since a half-life of a positron emitter produced by the nuclear reaction is long, it is inappropriate to check the distribution of the positron emitter in real time. Furthermore, there is little correlation between the dose distribution of the proton beam and a location at which the positron emitter is produced.

SUMMARY

The present disclosure provides a treatment apparatus using proton and ultrasound, capable of increasing the treatment effect and monitoring in real time with respect to a tumor.

The present disclosure also provides a method for treating cancer by using proton and ultrasound, capable of increasing the treatment effect and monitoring in real time with respect to a tumor.

The object of the present disclosure is not limited to the aforesaid, but other objects not described herein will be clearly understood by those skilled in the art from descriptions below.

An embodiment of the inventive concept provides a treatment apparatus using proton and ultrasound, the treatment apparatus including a proton generator configured to emit a proton beam to a tumor of a human body; an ultrasound generator configured to emit an ultrasonic beam to the tumor in a direction crossing an emission path of the proton beam; and a sensor configured to measure an acoustic signal generated during the emission of the proton beam.

In an embodiment, the treatment apparatus may further include a controller configured to calculate a stop point of the proton beam or an exposure dose of the proton beam, from the acoustic signal measured by the sensor.

In an embodiment, the proton generator may include a high power laser or a proton accelerator.

In an embodiment, the proton accelerator may include a synchrotron accelerator or a cyclotron accelerator.

In an embodiment, the ultrasound generator may be configured to emit the ultrasonic beam by using a transducer based on a piezoelectric element or a pulse laser.

In an embodiment, the treatment apparatus may further include an additional ultrasound generator for emitting an additional ultrasonic beam to the tumor, wherein the additional ultrasound generator is disposed to be spaced apart from the ultrasound generator so that a first emission path of the ultrasonic beam crosses a second emission path of the additional ultrasonic beam in a cross-section.

In an embodiment of the inventive concept, a method for treating cancer by using proton and ultrasound, the method includes: emitting an ultrasonic beam to a tumor of a human body; and emitting a proton beam to the tumor irradiated with the ultrasonic beam, wherein an emission paths of the ultrasonic beam and the proton beam cross each other in a cross-section.

In an embodiment, the proton beam may be emitted so that the proton beam has a stop location within the tumor, and the ultrasonic beam may be emitted so that the ultrasonic beam has a focal zone overlapping the stop location.

In an embodiment, the focal zone may have a width greater than that of the stop location.

In an embodiment, the focal zone may have a width equal to a distance between a point of the human body at which the proton beam initially arrives and the stop location.

In an embodiment, the focal zone may have a width equal to a distance between a point of the tumor at which the proton beam initially arrives and the stop location.

In an embodiment, the method may further include measuring an acoustic signal generated while the proton beam is emitted.

In an embodiment, the method may further include calculating an exposure dose of the proton beam and a stop point of the proton beam, from the measured acoustic signal.

In an embodiment, the method may further include emitting an additional ultrasonic beam to the tumor before the proton beam is emitted, wherein the emission paths of the ultrasonic beam and the additional ultrasonic beam cross each other in a cross-section.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Advantages and features of the present disclosure, and implementation methods thereof will be clarified through following embodiments described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the technical field to which the present disclosure pertains. Further, the present disclosure is only defined by scopes of claims. Like reference symbols refer to like elements throughout.

In this specification, the terms are used only for explaining embodiments while not limiting the present disclosure. In this specification, the singular forms are intended to include the plural forms as well, unless the context clearly indicates otherwise. It will be understood that the terms 'comprises' and/or 'comprising', when used in this specification, specify the presence of stated components, steps, operations and/or elements, but do not preclude the presence or addition of one or more other components, steps, operations and/or elements. Also, since preferred embodiments are provided below, the order of the reference numerals given in the description is not limited thereto.

Additionally, the embodiments described in this specification will be explained with reference to block diagrams, cross-sectional views, and/or flow charts as ideal exemplary views of the present disclosure. In the figures, the sizes and/or thicknesses of components are exaggerated for effectively describing the technical contents. Accordingly, shapes of the exemplary views may be modified according to manufacturing techniques and/or allowable errors. Therefore, the embodiments of the present disclosure are not limited to the specific shape illustrated in the exemplary views, but may include other shapes that may be created according to manufacturing processes. Therefore, the components exemplified in the drawings have general properties, and shapes of the components exemplified in the drawings are used to illustrate specific features of components in a device. Thus, this should not be construed as limited to the scope of the present disclosure.

Hereinafter, embodiments of the inventive concept will be described below in more detail with reference to the accompanying drawings.

Figure 1:
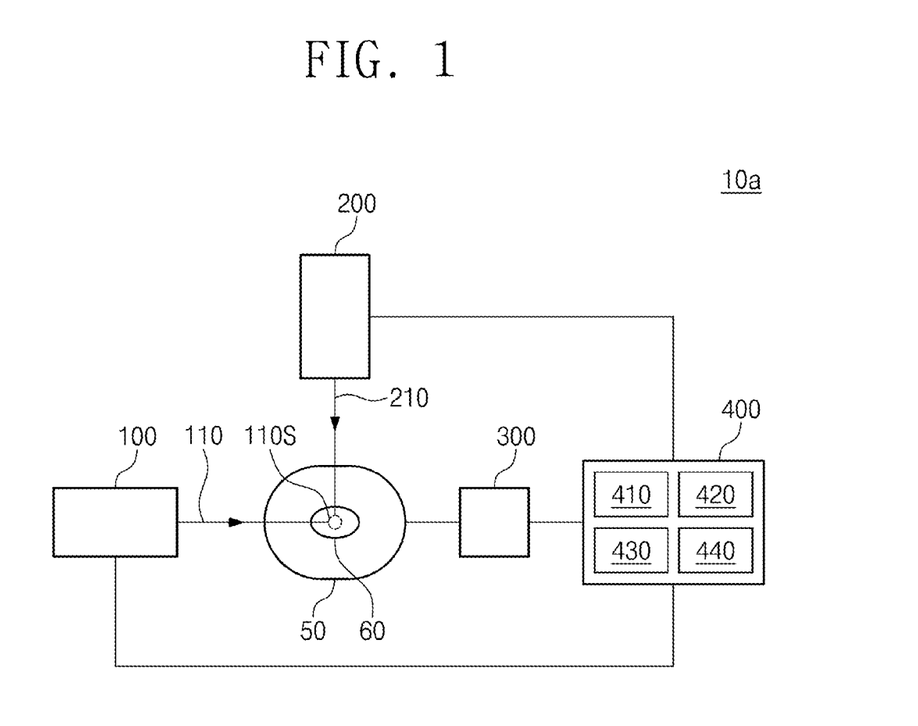
FIG. 1 is a schematic cross-sectional view for illustrating a configuration of a treatment apparatus using proton and ultrasound according to embodiments of the inventive concept.

FIG. 1 is a schematic cross-sectional view for illustrating a configuration of a treatment apparatus using proton and ultrasound according to an embodiment of the inventive concept.

Referring to FIG. 1, a treatment apparatus 10a using proton and ultrasound may include a proton generator 100, an ultrasound generator 200, a sensor 300, and a controller 400.

The proton generator 100 may emit a proton beam 110 to a tumor 60 in a human body 50. The tumor 60 may be, for example, a cancerous tissue. The proton generator 100 may include a high power laser or a proton accelerator. The proton accelerator may include, for example, a synchrotron accelerator or a cyclotron accelerator. The high power laser or the proton accelerator may adjust energy of a proton so that the proton beam 110 has the Bragg peak at a point where the tumor 60 in the human body 50 is located. The Bragg peak represents characteristics in which a proton rarely emits radiation when moving in a substance but emits radiation when staying in a substance. When the energy of the proton beam 110 is adjusted by considering a position where the proton beam 110 is emitted to the human body 50 and then stopped, the radiation is emitted to only the tumor 60 located at a specific place in the human body 50 to treat a cancer cell. Hereinafter, the position, at which the proton beam 110 is emitted to the human body 50 and then stopped, may referred to as a Bragg peak position 110S.

The location and size of the tumor 60 (for example, a length or a width) may be obtained from a treatment planning system, i.e., image diagnostic equipment such as a magnetic resonance imaging (MRI) apparatus, a computer tomography (CT) imaging apparatus, a positron emission tomography (PET) imaging apparatus, or an ultrasonic wave device. The energy of the proton beam 110 or the area irradiated by the proton beam 110 may be appropriately adjusted depending on a position, a size, or a state of the tumor 60.

The ultrasound generator 200 may emit an ultrasonic beam 210 to the tumor 60 in the human body 50. The ultrasound generator 200 may include, for example, an ultrasonic device based on a contact-type probe, or a laser ultrasonic device. The ultrasonic device based on the contact-type probe may use a transducer based on a piezoelectric element to emit the ultrasonic beam 210, and the laser ultrasonic device may use a pulse laser to emit the ultrasonic beam 210. During the emission of the ultrasonic beam 210, the ultrasound generator 200 may be closely attached to the human body 50 or spaced apart a predetermined distance from the human body 50. The ultrasonic beam 210 emitted from the ultrasound generator 200 may proceed in a direction crossing the emission path of the proton beam 110. That is, the emission path of the ultrasonic beam 210 may not be parallel with that of the proton beam 110. For example, the emission path of the ultrasonic beam 210 may be perpendicular to that of the proton beam 110, in a cross-section. Furthermore, the ultrasonic beam 210 may be a focused ultrasound. That is, the ultrasonic beam 210 may be focused on a focal zone to create a relatively narrow width (or a diameter), and then diffused. The focal zone of the ultrasonic beam 210 may overlap at least a portion of the tumor 60 and the Bragg peak position 110S.

The sensor 300 may measure an acoustic signal generated during the treatment of the tumor 60. For example, the sensor 300 may be an acoustic sensor. When the proton beam 110 is emitted to the inside of the human body 50, the acoustic signal may be generated by the interaction between a proton and an electron at the Bragg peak position 110S. In more detail, the proton that proceeds in the human body 50 may consistently loose kinetic energy, due to inelastic coulombic interactions with electrons around an atom. Through the inelastic coulombic interactions, there may be a phenomenon in which the electron obtains energy and then exits the atom while being scattering. When the electron obtains the energy, most of the energy is transformed into thermal energy. If a temperature change is induced at a specific location or space, a sound wave (i.e., an acoustic signal) spreading to the surroundings may be created. The sensor 300 may be closely attached to the human body 50 to measure the sound wave. For example, the sensor 300 may be closely attached to the human body 50, on the opposite side of the proton generator 100, to measure the sound wave.

The controller 400 may include a communication unit 410, a calculation unit 420, and a storage unit 430. The communication unit 410 may read data measured by the sensor 300. The calculation unit 420 may calculate an exposure dose of the proton beam 110 and the Bragg peak position 110S, by using the data that are read by the communication unit 410. The intensity of the acoustic signal measured by the sensor 300 may be a reference for calculating the exposure dose of the emitted proton beam 110 The time characteristics of the acoustic signal measured by the sensor 300 may be a reference for calculating the Bragg peak position 110S. For example, when the proton beam 110 is emitted into the human body 50, the acoustic signals generated from the Bragg peak position 110S reach the skin of the human body 50 while spreading in all directions. In this case, the Bragg peak position 110S may be accurately identified by physically contacting the sensor 300 (i.e., the acoustic sensor) to the skin to measure the acoustic signal, and then calculating a correlation between the time when the proton beam 110 initially arrives at the human body 50 and the time measured by the acoustic sensor while taking into consideration of propagation velocity of the acoustic signal in the human body.

The storage unit 430 may store an algorithm for the read and calculation, and the data (for example, the exposure dose of the proton beam and the Bragg peak position) calculated by the calculation unit 420. The data calculated by the calculation unit 420 may be transferred to the proton generator 100 or the ultrasound generator 200 through the communication unit 410. In addition, the controller 400 may further include an input/output unit 440. The input/output unit 440 may include a keyboard, a keypad, and/or a display device.

Figure 2:
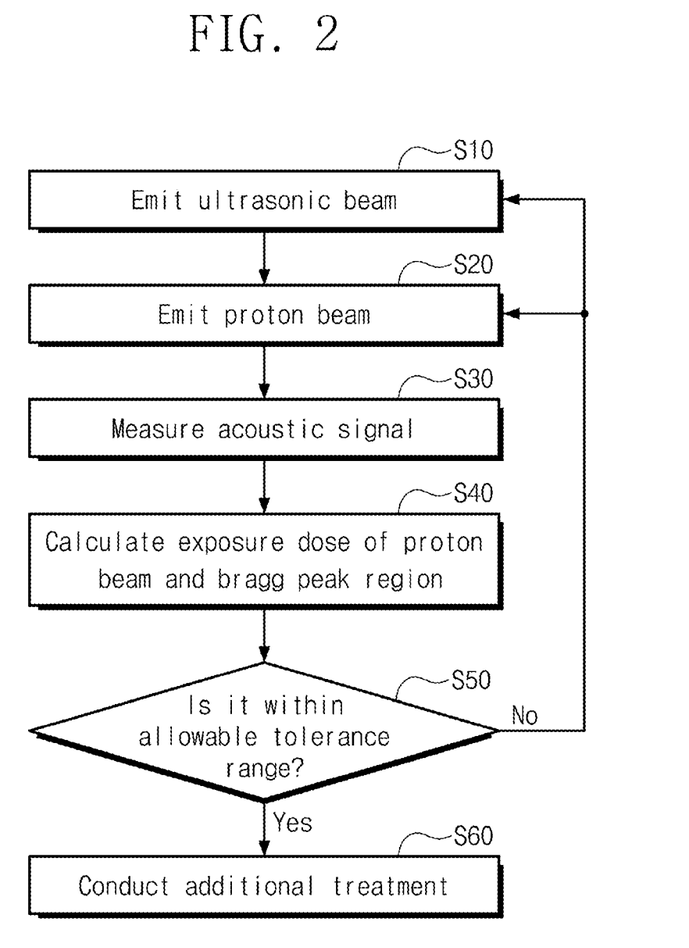
FIG. 2 is a flowchart for explaining a method for treating cancer by using the treatment apparatus of FIG. 1.

Hereinafter, a method for treating cancer by using the above-described treatment apparatus 10a will be explained. FIG. 2 is a flowchart for explaining a method for treating cancer by using the treatment apparatus of FIG. 1. FIGS. 3 to 7 are schematic conceptual views for explaining the method for treating cancer by using the treatment apparatus of FIG. 1.

Figure 3:
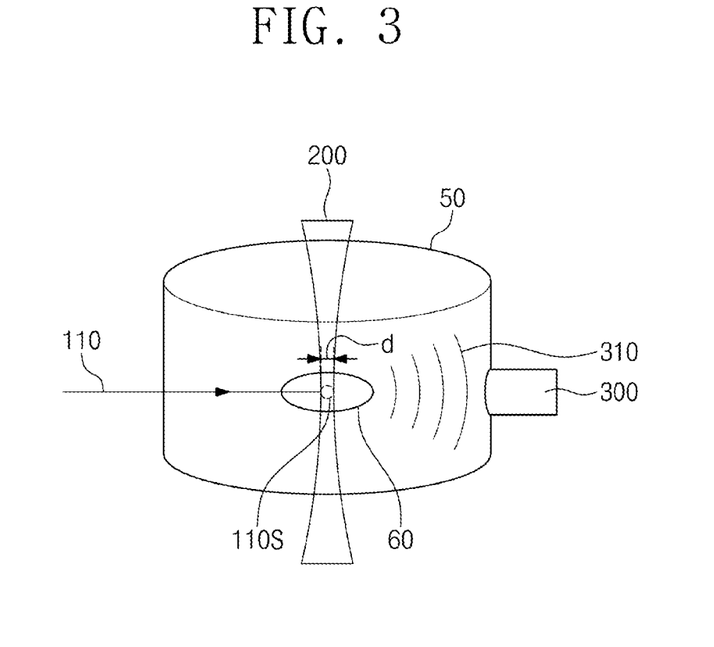
FIGS. 3 to 7 are schematic conceptual views for explaining the method for treating cancer by using the treatment apparatus of FIG. 1.

Referring to FIGS. 1 to 3, firstly, the ultrasonic beam 210 may be emitted to the tumor 60 of the human body 50 (S10). The ultrasonic beam 210 may be emitted into the human body 50 in a direction crossing a traveling path of the proton beam 110 emitted in a following step. Furthermore, the ultrasonic beam 210 may be focused on a location of the tumor 60, which is calculated by the treatment planning system (that is, on the Bragg peak position that is calculated by the treatment planning system). That is, the focal zone of the ultrasonic beam 210 may overlap at least a portion of the tumor 60. According to an embodiment, a width (d or a diameter) of the focal zone of the ultrasonic beam 210 may correspond to a width (or a diameter) of the Bragg peak position 110S. Hereinafter, the width (d or the diameter) of the focal zone of the ultrasonic beam 210 may be defined as the minimum width or the minimum diameter of the ultrasonic beam 210, which is measured in an emission direction of the proton beam 110. In a state in which only the ultrasonic beam 210 is emitted, a tumor portion on which the ultrasonic beam 210 is focused may receive more ultrasonic energy than other portions of the human body 50. Accordingly, a temperature of the tumor portion increases locally, and microbubbles may be created in the tumor portion. The microbubbles may provide the effect in that a rigid cancer tissue becomes loosened.

Then, the proton beam 110 may be emitted to the tumor 60 of the human body 50 (S20). The proton beam 110 may be emitted into the human body 50 in a direction crossing (for example, in a direction perpendicular to) the emission path of the ultrasonic beam 210. The emission paths of the ultrasonic beam 210 and the proton beam 110 may cross each other to thereby prevent or minimize the occurrence of a side effect in which a normal tissue is damaged. That is, the tumor 60, the focal zone of the ultrasonic beam 210, and the Bragg peak position 110S of the proton beam 110 may partially overlap each other. The energy of the proton beam 110 may be adjusted so that the proton beam 110 has a stop point (i.e., the Bragg peak position 110S) at a place in which the tumor 60 is located in the human body 60. While the proton beam 110 is emitted, the emission of the ultrasonic beam 210 may be stopped or continued.

The apoptosis of the cancer tissue (i.e., the tumor 60) may be induced by temperature rise of the tumor portion resulting from the emission of the ultrasonic beam 210 and microbubble oscillation resulting from the temperature rise. Also, the proton beam 110 subsequently emitted may accelerate the apoptosis process of the cancer tissue to maximize the treatment effect of the cancer tissue. Furthermore, the acoustic signal may be generated, through the interaction between the protons and the electrons, at the Bragg peak position 110S. The microbubbles generated by the ultrasonic beam 210 may amplify the acoustic signal.

The sensor may measure an amplified acoustic signal 310 (S30). The controller 400 may calculate the exposure dose of the proton beam 110 actually emitted and the Bragg peak position 110S, based on the intensity and the time characteristics of the measured acoustic signal (S40). Furthermore, the controller 40 may determine whether the differences between the estimated values of the exposure dose of the proton beam and the Bragg peak position according to the treatment plan and the real calculated values of the exposure dose of the proton beam and the Bragg peak region are within the allowable tolerance range (S50). When the difference values are within the allowable tolerance range, additional treatment according to the treatment plan may be conducted (S60). When the difference values are out of the allowable tolerance range, additional treatment according to the treatment plan may be conducted after energy or emission range of the proton beam 110 or the ultrasonic beam 210 is appropriately adjusted.

In the case of the cancer treatment by using only the proton beam, the types of proton beams to be used are generally limited, so the treatment effect by using the proton beam may be insufficient. Also, since intensities of the acoustic signal generated during the cancer treatment are not strong enough to be measured through the acoustic sensor, it may be difficult to accurately calculate the exposure dose of the proton beam and the Bragg peak position. However, when the treatment apparatus according to an embodiment of the inventive concept is used, the treatment effect of the tumor (i.e., the cancer tissue) may be maximized by the temperature rise around the tumor, resulting from the emission of the ultrasonic beam, and the creation of the microbubbles, in conjunction with the synergistic effect from the proton beam subsequently emitted. Furthermore, the exposure dose of the proton beam and the Bragg peak position may be monitored in real time to enable the more accurate and stable cancer treatment.

Also, the emission range of the ultrasonic beam 210 may be variously changed. This will be described below in detail with reference to FIGS. 4 and 7.

Figure 4:
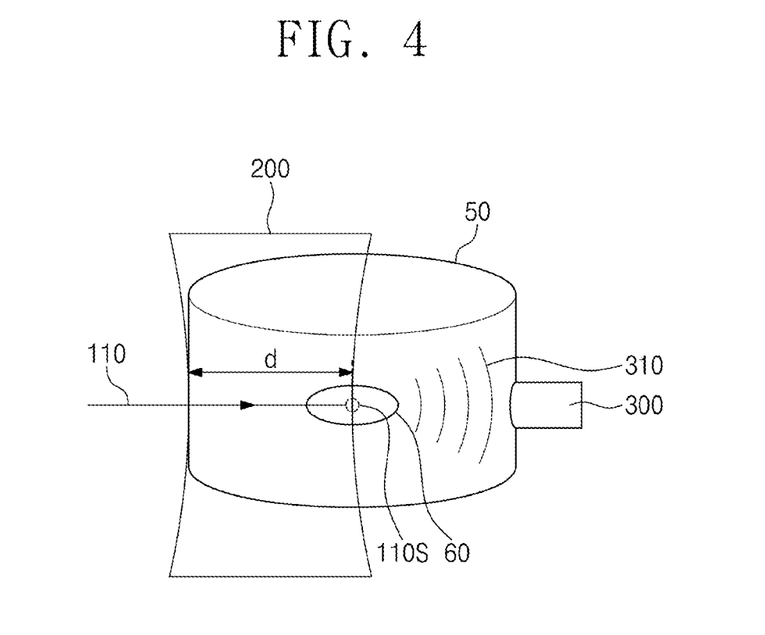

Referring to FIG. 4, the ultrasonic beam 210 may be emitted to the entire path of the proton beam 110 that passes through the human body 50 including the Bragg peak position 110S. For example, a width (d or a diameter) of a focal zone of an ultrasonic beam 210 may correspond to the distance between a point of the human body 50 at which the proton beam 110 initially arrives and the Bragg peak position 110S. In the treatment planning process prior to the cancer treatment, although the Bragg peak position 110S of the proton beam 110 can be calculated, an error may occur in the calculation when the proton beam 110 passes through the bones or the complex tissues. It may be difficult to expect the desired treatment and the monitoring effect, when the proton beam 110 arrives at other region although the ultrasonic beam 210 is emitted to the calculated Bragg peak region. Therefore, in this case, the ultrasonic beam 210 may be emitted to the entire area through which the proton beam 110 passes within the human body 50, as illustrated in FIG. 4.

Figure 5:
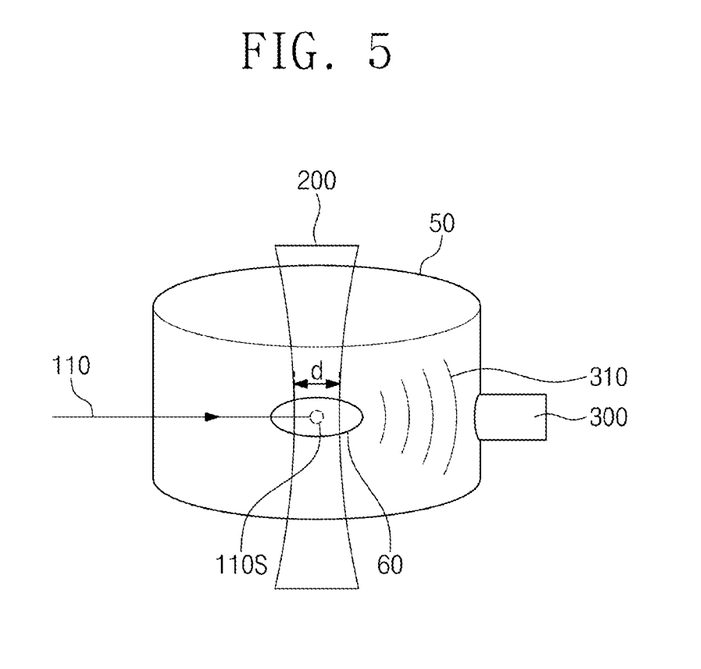

Referring to FIG. 5, when an error range of the Bragg peak region predicted by the treatment planning system is known, an ultrasonic beam 210 may be emitted across an area that is wider than the Bragg peak position 110S. For example, a width (d or a diameter) of a focal zone of the ultrasonic beam 210 may be greater than a width (or a diameter) of the Bragg peak position 110S.

Figure 6:
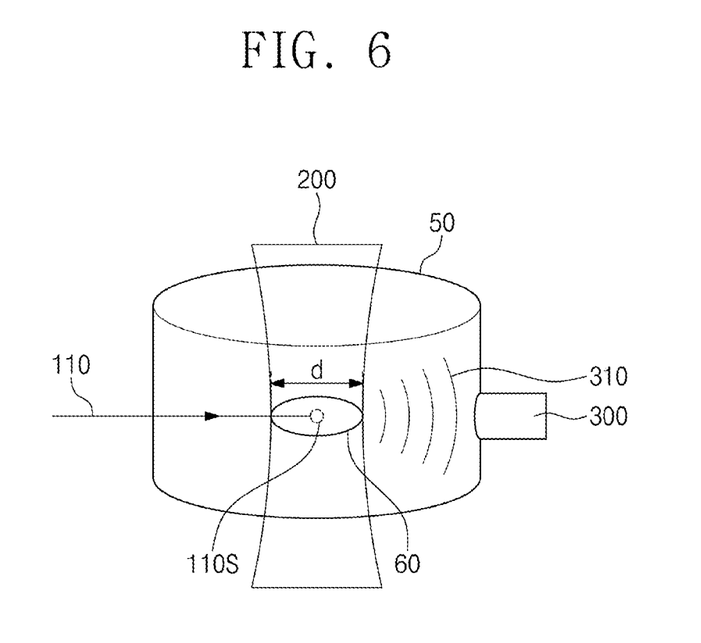
Figure 7:
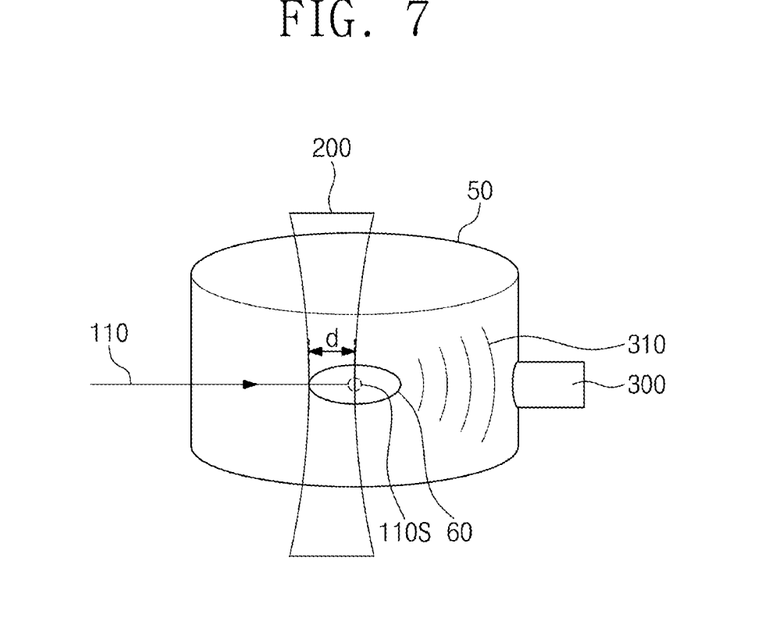

Referring to FIGS. 6 and 7, when the tissue or the organ which are easily damaged by a strong ultrasonic beam are located at a path through which the proton beam 110 passes, an ultrasonic beam 210 may not be emitted to a path before the proton beam 110 arrives at the tumor 60, unlike the case of FIG. 4. For example, as illustrated in FIG. 6, an ultrasonic beam 210 may be emitted to the entire area of the tumor 60 including an area through which the proton beam 110 passes within the tumor 60. That is, a width (d or a diameter) of a focal zone of the ultrasonic beam 210 may correspond to the length of the tumor 60 according to the emission direction of the proton beam 110. For another example, an ultrasonic beam 210 may be emitted to overlap an area through which the proton beam 110 passes within the tumor 60. That is, a width (d or a diameter) of a focal zone of the ultrasonic beam 210 may correspond to the distance between a point of the human body 60 at which the proton beam 110 initially arrives and the Bragg peak position 110S.

Figure 8:
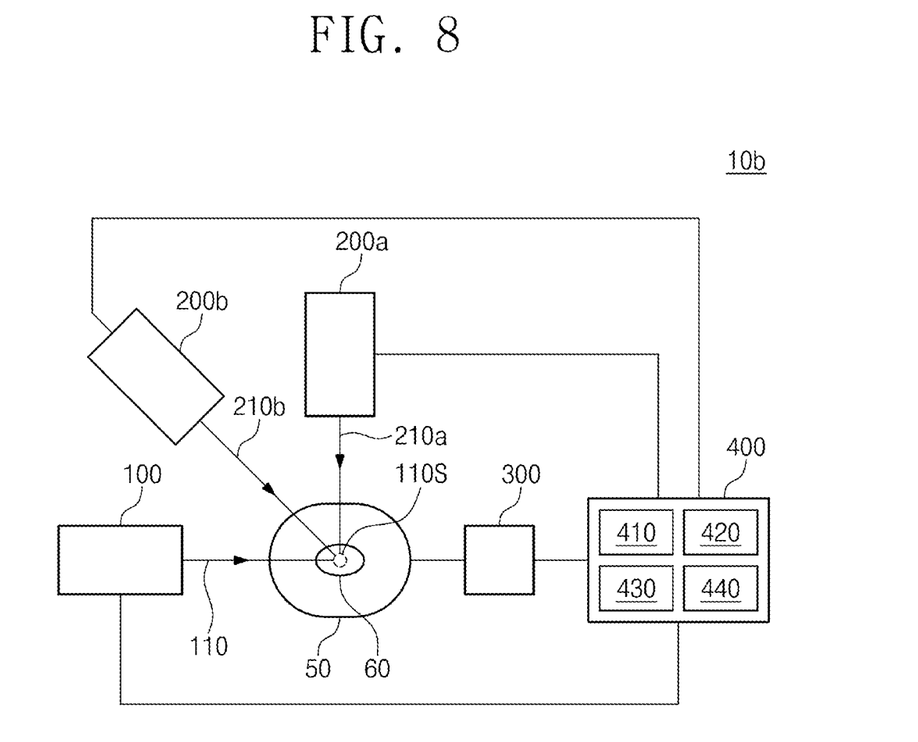
FIG. 8 is a schematic cross-sectional view for illustrating a configuration of a treatment apparatus using proton and ultrasound according to other embodiments of the inventive concept.
Figure 9:
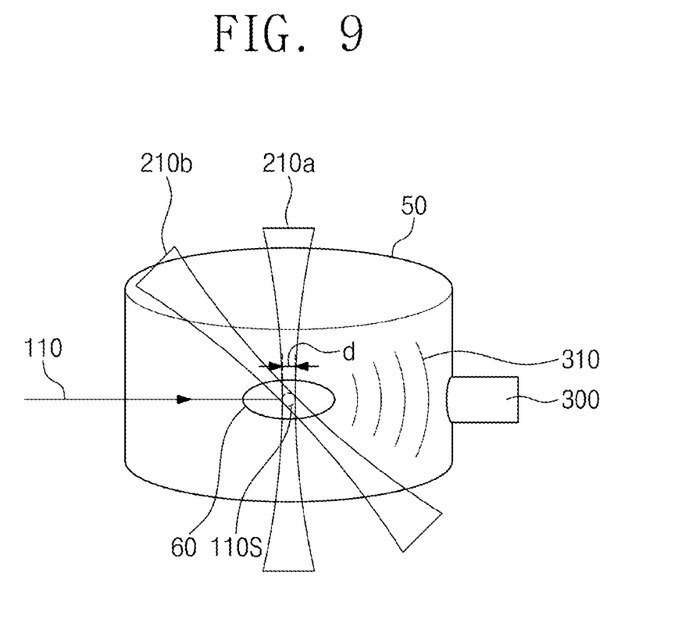
FIG. 9 is a schematic conceptual view for explaining a method for treating cancer by using the treatment apparatus of FIG. 8.

FIG. 8 is a schematic cross-sectional view for illustrating a configuration of a treatment apparatus using proton and ultrasound according to other embodiments of the inventive concept. FIG. 9 is a schematic conceptual view for explaining a method for treating cancer by using the treatment apparatus of FIG. 8. For simplification of description, the differences with respect to the treatment apparatus 10a of FIG. 1 and the method for treating cancer by using the same will be mainly described, and detailed descriptions for duplicated features will be omitted.

Referring to FIGS. 8 and 9, a treatment apparatus 10b using proton and ultrasound may further include an additional ultrasound generator. That is, ultrasound generators of the treatment apparatus 10b may include a first ultrasound generator 200a and a second ultrasound generator 200b. The first and second ultrasound generators 200a and 200b may have the substantially same structure as the ultrasound generator 200 of FIG. 1.

The first and second ultrasound generator 200a and 200b respectively emit ultrasonic beams 210a and 210b, which are emitted to the tumor 60 in the human body 50, while crossing each other at a predetermined angle. That is, the second ultrasound generator 200b may be disposed to be spaced apart from the first ultrasound generator 200a so that the emission paths of the first ultrasonic beam 210a and the second ultrasonic beam 210b cross each other in a cross-section. In addition, the emission paths of the ultrasonic beams 210a and 210b may cross the emission path of the proton beam 110. When the two ultrasonic beams 210a and 210b cross each other at the predetermined angle, interference patterns corresponding to the crossing angle may be generated. The locations at which the interference patterns are created may be determined by the phase difference between the two ultrasonic beams 210a and 210b, and the distances between the interference patterns may change depending on the crossing angle. At the crossing areas of the interference patterns, a portion in which the constructive interference occurs may receive stronger ultrasonic energy than other portions. In this case, when the phases between the ultrasonic beams 210a and 210b are changed, the interference patterns may be moved in a specific direction. Accordingly, the crossing areas of the interference patterns may evenly overlap the tumor 60 to increase the average energy of the ultrasonic beam emitted to the tumor 60. The treatment apparatus 10b according to an embodiment of the inventive concept may be used in the case that strong ultrasonic energy is required depending on biochemical or physical characteristics of the tumor 60, and in the case that the intensity of the acoustic signal generated from the Bragg peak position 110S is weak when the proton beam 110 is emitted.

When the treatment apparatus according to an embodiment of the inventive concept is used, the treatment effect of the tumor (i.e., the cancer tissue) may be maximized by the temperature rise around the tumor, resulting from the emission of the ultrasonic beam, and the creation of the microbubbles, in conjunction with the synergistic effect from the proton beam subsequently emitted. Furthermore, the exposure dose of the proton beam and the Bragg peak position may be monitored in real time to enable the more accurate and stable cancer treatment.

Although the embodiments of the inventive concept are described with reference to the accompanying drawings, those with ordinary skill in the technical field to which the inventive concept pertains will understand that the present disclosure can be carried out in other specific forms without changing the technical idea or essential features. Therefore, the above-disclosed embodiments are to be considered in all aspects as illustrative and not restrictive.

What is claimed is:

1. A treatment apparatus using proton and ultrasound, the treatment apparatus comprising:
   a proton generator configured to emit a proton beam to a tumor of a body;

an ultrasound generator configured to emit an ultrasonic beam to the tumor in a direction crossing an emission path of the proton beam; and a sensor configured to measure an acoustic signal generated during the emission of the proton beam, wherein the proton beam is configured to emit so that the proton beam has a stop location within the tumor, and wherein the ultrasonic beam is configured to emit so that the ultrasonic beam has a focal zone overlapping the stop location.

2. The treatment apparatus of claim 1, further comprising a controller configured to calculate a stop point of the proton beam or an exposure dose of the proton beam, from the acoustic signal measured by the sensor.

3. The treatment apparatus of claim 1, wherein the proton generator comprises a high power laser or a proton accelerator.

4. The treatment apparatus of claim 3, wherein the proton accelerator comprises a synchrotron accelerator or a cyclotron accelerator.

5. The treatment apparatus of claim 1, wherein the ultrasound generator is configured to emit the ultrasonic beam by using a transducer based on a piezoelectric element or a pulse laser.

6. The treatment apparatus of claim 1, further comprising an additional ultrasound generator for emitting an additional ultrasonic beam to the tumor, wherein the additional ultrasound generator is disposed to be spaced apart from the ultrasound generator so that a first emission path of the ultrasonic beam crosses a second emission path of the additional ultrasonic beam in a cross-section.

7. The treatment apparatus of claim 1, wherein the body is a human body.

8. A method for treating cancer by using proton and ultrasound, the method comprising:

emitting an ultrasonic beam to a tumor of a body; and emitting a proton beam to the tumor irradiated with the ultrasonic beam, wherein emission paths of the ultrasonic beam and the proton beam cross each other in a cross-section, wherein the proton beam is emitted so that the proton beam has a stop location within the tumor, and wherein the ultrasonic beam is emitted so that the ultrasonic beam has a focal zone overlapping the stop location.

9. The method of claim 8, wherein the focal zone has a width greater than that of the stop location.

10. The method of claim 8, wherein the focal zone has a width equal to a distance between a point of the body at which the proton beam initially arrives and the stop location.

11. The method of claim 8, wherein the focal zone has a width equal to a distance between a point of the tumor at which the proton beam initially arrives and the stop location.

12. The method of claim 8, further comprising measuring an acoustic signal generated while the proton beam is emitted.

13. The method of claim 12, further comprising calculating an exposure dose of the proton beam and a stop point of the proton beam, from the measured acoustic signal.

14. The method of claim 8, further comprising emitting an additional ultrasonic beam to the tumor before the proton beam is emitted, wherein the emission paths of the ultrasonic beam and the additional ultrasonic beam cross each other in a cross-section.

15. The method of claim 8, wherein the body is a human body.

* * * * *